United States Patent [19]

Grafelmann et al.

[11] 4,406,623

[45] Sep. 27, 1983

[54] SCREW-TYPE BONE IMPLANT FOR RECEIVING A DENTAL PROSTHESIS

[76] Inventors: Hans L. Grafelmann, Parkstrasse 105, D-2800 Bremen 1, Fed. Rep. of Germany; Dino Garbaccio, Via Marconi 7, Biella (Vercelli), Italy

[21] Appl. No.: 329,814

[22] Filed: Dec. 11, 1981

[30] Foreign Application Priority Data

Jan. 9, 1981 [IT] Italy .............................. 19199 A/81
Mar. 23, 1981 [IT] Italy ............................. 21181/81[U]

[51] Int. Cl.³ .............................................. A61C 8/00
[52] U.S. Cl. ................................................... 433/174
[58] Field of Search ............................ 433/174, 172

[56] References Cited

U.S. PATENT DOCUMENTS 3,672,058  6/1972  Nikoghossian ...................... 433/174
4,103,422  8/1978  Weiss et al. ......................... 433/174

FOREIGN PATENT DOCUMENTS 2395738  7/1977  France ............................... 433/174

Primary Examiner—Robert Peshock
Attorney, Agent, or Firm—Pearne, Gordon, Sessions, McCoy, Granger & Tilberry

[57] ABSTRACT

A screw-type bone implant is disclosed having a shaft which, because of the design of its thread and because of its length and the design of its free end, is supported after implantation between its two ends by compact bone substance, and which is, immediately after the implantation, surrounded between its two ends by spongelike bone substance, so that the implant offers a permanent and particularly secure support for a dental prosthesis.

11 Claims, 3 Drawing Figures

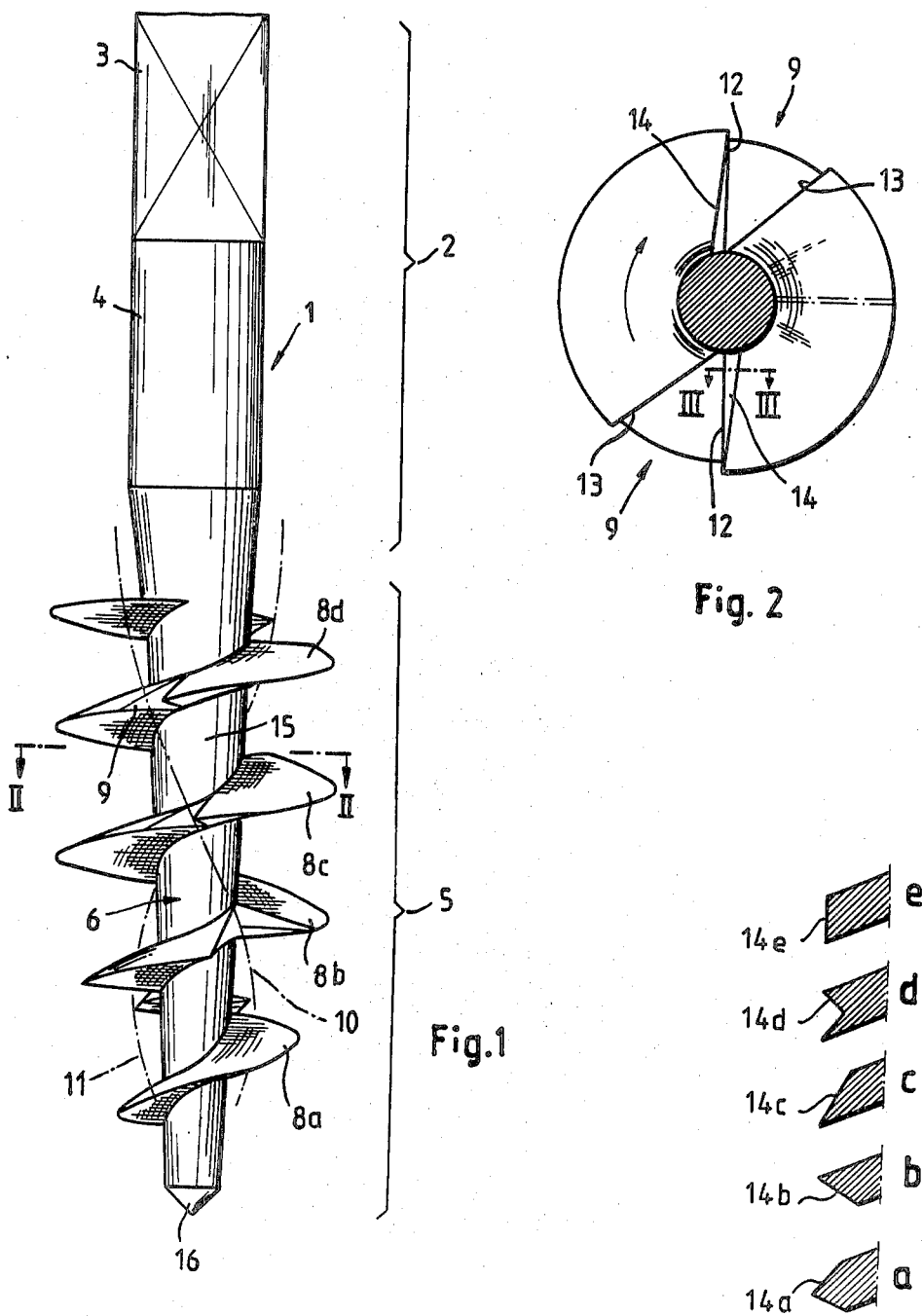

SCREW-TYPE BONE IMPLANT FOR RECEIVING A DENTAL PROSTHESIS

BACKGROUND OF THE INVENTION

This invention relates to a screw-type bone implant with a shaft, which is designed at one extremity to receive a dental prosthesis, which ends freely at its other extremity, and which has a threaded helix between the two extremities.

Bone implants for screwing into the jawbone onto which is subsequently mounted a dental prosthesis have been known for some time in a multiplicity of designs.

It is clear that a bone implant must be long-lasting and, accordingly, must support the dental prosthesis for as long a period as possible. In order to attain this goal, new proposals have continuously been submitted. From the abundance of examples, reference is made to German Patent Application (Offenlegungschift) No. 2,255,916, No. 2,540,077, and No. 2,628,443, which all disclose bone implants in the form of screw-type devices which consist in part of ceramics and in part of metal, and which are subdivided into a threaded section and a fastening section.

Despite the abundance of attempts toward creating a permanent bone implant, the results have not been satisfactory in all respects. It is therefore an object of this invention to provide a screw-type bone implant which represents an improvement over the prior art, primarily through greater sturdiness in the implanted condition.

This invention provides a screw-type implant of the originally mentioned type which solves this task, and in which the length of the shaft is greater by at least the axial length of the head which receives the dental prosthesis than the height of the jawbone viewed in the direction into which the implant is made. There are V-shaped cutouts in the threads of the threaded helix at distances along the arc of the helix which are smaller than 360 degrees and which are other than 180 degrees. The cutouts extend from the circumference of the helix and have tips which are positioned in the area of the shaft surface. Each cutout has two sides forming two contact surfaces which lie substantially in the longitudinal direction of the shaft. The contact surface having the greater distance from the free shaft end is provided with at least one protruding sharp edge extending in the direction of the thread. The external diameter of the threaded helix increases in axial direction from the free end of the shaft to a large final value.

It is advantageous in this instance to provide the free end of the shaft with the shape of a pointed cone.

Whereas, to implant the known screw-type implant it was necessary to initially pre-drill a hole having an external diameter almost equal to the external diameter of the implant threading, to implant the implant according to this invention it is only necessary to pre-drill a hole having the diameter of the shaft, inasmuch as the implant of this invention will cut the threading by itself.

The known screw-type device for implants could be kept in place only when bone matter had grown in and, immediately after implantation, a comparatively large hollow space remained from the small threading region radially inwardly toward the shaft, which space was only gradually filled in with growing bone substance. The known implants, therefore, could be initially subjected to only comparatively minor stresses. In addition, the initial, less-than-optimum anchoring of the implant in the spongelike substance of the bone resulted in the phenomenon that the implant could move, not only axially but also radially, when stresses were applied. This movement would naturally tend to impede the growing-in process and favor formation of soft bone replacement tissue or granulation tissue.

With the implant according to this invention, these difficulties no longer occur because no hollow spaces have to be filled in before the implant can be exposed to stress, and primarily also because of the length of the implant, so that when it is screwed into the jawbone, the implant is supported at both ends within the bone, i.e., at the entrance and at its free end, so that the implant supports itself after penetration of the spongelike substance on the compact bone substance which lies opposite the entrance. Thus, from the very beginning, axial as well as radial movement of the implant is practically impossible, whereby the initial healing process can take place without interference, and whereby durability is significantly enhanced.

A further consequence of the self-cutting capability of the bone implant according to this invention is that a portion of the bone substance need not be permanently removed. The implant can be squeezed into existing hollow spaces of the spongelike bone substance, and these portions of the bone substance can be better supplied with blood because of the lessened trauma. Thus, weakening of the jawbone is reduced.

In summary, the teaching of the invention provides that only a minimum of bone substance must be removed, namely, the volume of the implant shaft, while the threads completely and automatically cut their own path. Thus, the finished implant, from the very beginning, is embedded more evenly and more firmly in the jawbone than was hitherto possible. The formation of new bone substance, which is less able to withstand pressure than the original bone substance, will no longer occur because no empty cavities remain.

BRIEF DESCRIPTION OF THE DRAWINGS

In the following, the invention is explained in detail, based on the preferred embodiment which is illustrated in the drawings. The following illustrations are shown in enlarged scale:

FIG. 1 is a lateral view of the bone implant;

FIG. 2 is a cross section through the implant, taken through line II—II of FIG. 1; and FIG. 3 is a series of sections, taken along line III—III of FIG. 2, each illustrating different shapes of the sharp edge at the various locations.

DETAILED DESCRIPTION OF THE PREFERRED EMBODIMENT

Referring to FIG. 1, a bone implant 1 has a shaft 6 which is divided into a total of four axially successive portions. The first portion is formed by a head 3 which has a square cross section and which thus forms the application points for a tool which is used to screw in the implant and for the dental prosthesis which is to be mounted later. After this first portion, there follows a cylindrical portion 4, a conical portion 15 which tapers slightly away from the head 3, and, finally, a support 16 at the free end of the shaft 6. This support 16 is formed in the preferred embodiment at the free end of shaft 6 in the shape of a cone, ending in a point. The preferred angle of aperture of the cone is around 90 degrees. In an alternate embodiment, the free end of the shaft may be shaped like a semisphere.

A part 2 of the implant 1 formed by the first and second portions of the shaft 6 is located essentially outside the bone after implantation, whereas, the remaining part 5 formed by the other two portions of the shaft is positioned within the bone.

The conical portion 15 of the shaft is provided with a threaded helix 8 which, in the preferred embodiment when viewed in the axial direction of the shaft, begins at a distance spaced from the support 16 and ends before the cylindrical portion 4. As can clearly be seen fron FIG. 1, the diameter of the threaded helix 8, when viewed from support 16, increases over several threads 8a, 8b, and 8c, and then remains constant, as can be seen by comparing the threads 8c and 8d. It will be noted that the increase in the diameter of the threaded helix 8 is greater than the equidirectional diameter increase of the conical portion 15. It is preferable that the increase in the diameter of the threaded helix not be constant but, rather, that it decrease in the direction toward the head 3, as is observed when comparing the threads 8a and 8b or when comparing the threads 8b 8c of FIG. 1. The maximal diameter of the threaded helix, for example, in the area of the thread 8d is approximately twice as large as the diameter of the cylindrical portion 4.

Beginning at its exterior circumference, the threaded helix 8 is equipped with V-shaped cutouts 9, which extend essentially in the radial direction. In the preferred embodiment, the point of each V is positioned on the surface of the conical portion 6. These cutouts 9 are distributed over the entire length of the threaded helix 8 in such a manner that, when viewed in axial direction, each cutout 9 is covered by the thread which is positioned either above or below. In other words, the cutouts 9, when the threads are viewed in the axial direction, are not in alignment with each other. This is achieved by the fact that the cutouts 9 follow each other at arc distances which are smaller than 360 degrees, but which are not 180 degrees. The position of the cutouts 9 is indicated in FIG. 1 by the two broken lines 10 and 11, which run in the shape of a spiral. The direction of the spiral of the two lines 10 and 11 is opposite to the direction of the spiral of the threaded helix 8.

It can be ascertained from FIGS. 1 and 2 that each cutout 9 exhibits two contact surfaces 13 and 14, i.e., areas through which the thread is cut off. As a result of these two contact surfaces 13 and 14, the contact surface 14, which is in each case farther from the support 16, is provided with a sharp edge 12 which effects the cutting of the bone implant into the jawbone. When viewed from the center of the shaft, the contact surface 14, which is provided with the sharp edge 12, runs substantially radially from the shaft surface to the outside. In the illustrated example, the radial direction is exactly true for the sharp edge 12, while it is only approximately true for the contact surface 14 itself. The other contact surface 13 in each case extends with respect to the exact radial direction in leading manner towards the outside in the direction of the thread, which can clearly be recognized from the plan view of FIG. 2. Looking at the edges of contact surfaces 13 and 14 of FIG. 2, which are positioned in the plane of the paper, it will be recognized that these surfaces essentially form an angle of approximately 45 degrees.

FIG. 3 illustrates various design possibilities of the sharp edge of contact surface 14. In FIG. 3a, the sharp edge is positioned in the center relative to the thickness of the thread. In FIG. 3b, the sharp edge is positioned on the edge between contact surface 14b and the surface of the thread positioned above. FIG. 3c illustrates the reverse of the design according to FIG. 3b. In FIG. 3d, there are two sharp edges which are formed by a notch in the contact surface 14d and which are positioned at the upper and at the lower edge of the thread. FIG. 3e basically corresponds to the design in accordance with FIG. 3c, except for a smaller cutting angle.

Other modifications and variations in the specific product herein shown and described will be apparent to those skilled in the art all within the intended scope and spirit of the invention. While the invention has been shown and described with respect to a specific embodiment thereof, this is intended for the purpose of illustration rather than limitation. Accordingly, the patent is not to be limited to the specific embodiment herein shown and described, nor in any other way that is inconsistent with the extent to which the progress in the art has been advanced by the invention.

What is claimed is:

1. An improved screw-type bone implant of the type having a shaft, which has at its one extremity a head for receiving a dental prosthesis, which ends freely at its other extremity, and which has a threaded helix between the two extremities, wherein the improvement comprises:

the length of the shaft being longer by at least the axial length of the head than the height of the jawbone into which the implant is to be effected, when viewed in the direction of the implantation;

there being V-shaped cutouts in the threads of the threaded helix, at distances along the arc of the helix of an aliquant part of about 360 degrees, the cutouts extending from the circumference of the helix in a generally radial direction, each cutout having a tip which lies at the shaft surface;

each cutout having two sides each forming contact surfaces which are substantially positioned in the longitudinal direction of the shaft, the contact surface with the greater distance from the free end of the shaft provided with at least one sharp edge which protrudes into the cutout; and the external diameter of the threaded helix when considered from the free end of the shaft in an axial direction increasing from a small initial value to a large final value.

2. An improved implant according to claim 1, wherein the helix comprises, in addition to the first group of cutouts, a second group of identical cutouts recessed and arranged with respect to the first group in a staggered fashion.

3. An improved implant according to claim 1, wherein at least a portion of the shaft before its free end is frustoconical shaped.

4. An improved implant according to claim 1, 2, or 3, wherein the free end of the shaft is shaped like a pointed cone.

5. An improved implant according to claim 4, wherein the aperture angle of the cone is approximately 90 degrees.

6. An improved implant according to claim 1, wherein the largest external diameter of the threaded helix is approximately twice as large as the largest diameter of the shaft.

7. An improved implant according to claim 1, wherein the sharp edge extends radially towards the shaft.

8. An improved implant according to claim 1, wherein the V-shape of each of the cutouts has an aperture angle of approximately 45 degrees.

9. An improved implant according to claim 1, wherein the contact surfaces of the V-shaped cutouts are of unequal lengths.

10. An improved implant according to claim 9, wherein the longer contact surface of each cutout extends in the longitudinal direction of the shaft to the sharp edge.

11. An improved implant according to claim 1, 8, or 9, wherein a line bisecting the angle of each V-shaped cutout crosses the cross-sectional area of the shaft as a chord, and said bisecting line leads a shaft radius which crosses the top of the cutout in the direction of the screw thread of the implant.

* * * * *

UNITED STATES PATENT AND TRADEMARK OFFICE
CERTIFICATE OF CORRECTION

PATENT NO.  : 4,406,623
DATED       : September 27, 1983
INVENTOR(S) : Hans L. Grafelmann, et al.

It is certified that error appears in the above—identified patent and that said Letters Patent is hereby corrected as shown below:

Column 1, line 19, delete "Application" and insert --Applications--.

Column 3, line 21, after "8b" (second occurrence), insert --and--.

Signed and Sealed this

Thirteenth Day of March 1984

[SEAL]

Attest:

GERALD J. MOSSINGHOFF

Attesting Officer

Commissioner of Patents and Trademarks